(12) United States Patent
Langes et al.

(10) Patent No.: US 10,703,750 B2
(45) Date of Patent: Jul. 7, 2020

(54) CRYSTALLINE VALBENAZINE FREE BASE

(71) Applicant: Sandoz AG, Basel (CH)

(72) Inventors: Christoph Langes, Innsbruck (AT); Stefan Reissmann, Bitterfeld-Wolfen (DE)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 16/462,358

(22) PCT Filed: Dec. 6, 2017

(86) PCT No.: PCT/EP2017/081678
§ 371 (c)(1),
(2) Date: May 20, 2019

(87) PCT Pub. No.: WO2018/130345
PCT Pub. Date: Jul. 19, 2018

(65) Prior Publication Data
US 2019/0315744 A1 Oct. 17, 2019

(30) Foreign Application Priority Data

Jan. 10, 2017 (EP) .................................... 17150904

(51) Int. Cl.
*C07D 471/04* (2006.01)
(52) U.S. Cl.
CPC ........ *C07D 471/04* (2013.01); *C07B 2200/13* (2013.01)

(58) Field of Classification Search
CPC .......................... C07D 471/04; C07B 2200/13
See application file for complete search history.

(56) References Cited

U.S. PATENT DOCUMENTS

2017/0145008 A1* 5/2017 McGee ................ C07D 471/04

FOREIGN PATENT DOCUMENTS

| WO | 2008058261 A1 | 5/2008 |
|---|---|---|
| WO | 2010044981 A3 | 6/2010 |
| WO | 2011153157 A2 | 12/2011 |
| WO | 2014120654 A1 | 8/2014 |
| WO | 2015084622 A1 | 6/2015 |
| WO | 2015171802 A1 | 11/2015 |
| WO | 2017075340 A1 | 5/2017 |
| WO | 2017112857 A1 | 6/2017 |

OTHER PUBLICATIONS

International Search Report and Written Opinion for PCT/EP2017/081678, dated Jul. 19, 2018, 10 pages.

* cited by examiner

*Primary Examiner* — Timothy R Rozof
(74) *Attorney, Agent, or Firm* — Luedeka Neely Group, P.C.

(57) ABSTRACT

The present disclosure generally relates to crystalline valbenazine. The present disclosure also generally relates to a pharmaceutical composition comprising crystalline valbenazine, as well of methods of using crystalline valbenazine in the treatment of hyperkinetic disorders, and methods for obtaining such forms.

11 Claims, 2 Drawing Sheets

CRYSTALLINE VALBENAZINE FREE BASE

This application is a Section 371 national phase entry of PCT application PCT/EP2017/081678, filed Dec. 6, 2017. This application also claims the benefit of the earlier filing date of European patent application 17150904.5, filed Jan. 10, 2017.

FIELD OF INDUSTRIAL APPLICABILITY

The present disclosure generally relates to crystalline valbenazine. The present disclosure also generally relates to a pharmaceutical composition comprising crystalline valbenazine, as well of methods of using crystalline valbenazine in the treatment of hyperkinetic disorders, and methods for obtaining such forms.

BACKGROUND OF THE DISCLOSURE

The vesicular monoamine transporter (VMAT) is a transport protein integrated into the membrane of synaptic vesicles of presynaptic neurons. It acts to transport monoamine neurotransmitters—such as dopamine, serotonin, norepinephrine, epinephrine, and histamine—into the vesicles, which release the neurotransmitters into synapses as chemical messages to postsynaptic neurons. Pharmaceutical drugs that target VMATs have possible applications for many conditions. These applications include hypertension, drug addiction, psychiatric disorders, Parkinson's disease, and other neurological disorders. There are two types of VMATs expressed in humans: VMAT1 and VMAT2.

The vesicular monoamine transporter 2 (VMAT2) also known as solute carrier family 18 member 2 (SLC18A2) is a protein that in humans is encoded by the SLC18A2 gene. VMAT2 transports monoamines—particularly neurotransmitters such as dopamine, norepinephrine, serotonin, and histamine—from cellular cytosol into synaptic vesicles. If VMAT2 function is inhibited or compromised, such neurotransmitters cannot be released via normal transport (exocytosis, action potential) into the synapse.

The compound Valbenazine is a highly selective, small-molecule vesicular monoamine transporter 2 (VMAT2) inhibitor being developed by Neurocrine Biosciences for the treatment of a variety of central nervous system disorders, such as involuntary hyperkinetic movement disorders including drug-induced tardive dyskinesia and Tourette's syndrome. It is known that Valbenazine regulates levels of dopamine release during nerve communication, but has minimal impact on other monoamines, which may help to reduce the likelihood of "off-target" side effects. Valbenazine is in phase III development for drug-induced dyskinesia in patients with schizophrenia or schizoaffective disorder. Phase II development is underway for the treatment of adult patients with Tourette's syndrome. Furthermore, preclinical studies in models of schizophrenia is underway. Valbenazine may be useful in other disorders such as Huntington's disease and tardive dystonia.

Valbenazine has the chemical name (S)-2-Amino-3-methyl-butyric acid, (2R,3R,11bR)-3-isobutyl-9,10-dimethoxy-1,3,4,6,7,11b-hexahydro-2H-pyrido[2,1-a]isoquinolizin-2-yl ester. It is also known as NBI-98854 and has the following chemical structure according to Formula I:

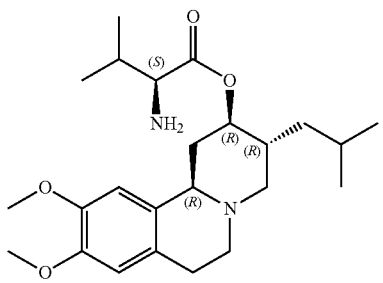

Formula I

WO 2008/058261 A1 discloses the production of valbenazine as free compound (compound 2-1 in Example 2). The document further discloses the administration of single oral doses of valbenazine in 10% PEG in 0.25% methylcellulose in milli Q water to rats for a pharmacokinetic evaluation (Example 6). The document discloses a composition formulated as liquid solution which is often inconvenient or even unacceptable for use in a pharmaceutical product. There is thus a need for useful alternatives to the liquid compositions disclosed in WO 2008/058261 A1.

Nowadays, one of the most common dosage forms produced by pharmaceutical industries and preferred by the majority of patients are oral dosage forms (such as tablets or capsules). They are more preferable than any other dosage form as they are taken orally by patients, which is a convenient and safe way of drug administration and are more stable compared to liquids (physical and chemical stability). Different types of oral dosage forms require a different formulation in order to be produced as each category has different properties, and alterations may be needed in the choice of excipients and choice of the solid form of the active ingredient each time. That means that every oral dosage form is a different situation.

WO 2015/171802 A1 discloses oral administration of valbenazine to patients (Example 2). According to page 16, lines 16-17 of the document, valbenazine is preferably used in form of its dihydrochloride or ditosylate salt. Different salts and solid state forms (including solvated forms) of an active pharmaceutical ingredient often possess different properties. There is still a need for useful alternatives to the dihydrochloride and ditosylate salt disclosed in WO 2015/171802 A1.

New salts, solid state forms and solvates of an active pharmaceutical ingredient may have desirable or even improved processing properties compared to known salts, solid state forms and solvates. New salts, solid state forms and solvates of an active pharmaceutical ingredient may be easy to handle during the production or formulation process, suited for storage, allow purification or allow conversion to even further salts or polymorphic forms. Such properties of different salts and solid state forms and solvates in turn can allow desirable pharmaceutical formulations, for example, formulations with a desirable dissolution profile, or with desirable stability and shelf-life. Compared to known salts, solid state forms and solvates, new salts, solid state forms and solvates of an active pharmaceutical ingredient may also show improved properties during production or formulation process, or in the formulation.

In particular, there is still a need for a further solid state form of the active pharmaceutical ingredient valbenazine which form has one or more of the above-indicated desirable or improved properties. There is also a need for a further pharmaceutical composition containing such a solid state form of the active pharmaceutical ingredient valbenazine which composition has one or more of the above-indicated desirable properties.

SUMMARY OF THE DISCLOSURE

It was an objective of the current invention to provide new means of improving the properties of valbenazine, especially in regard to the treatment of hyperkinetic disorders, by providing new drugable forms of valbenazine.

The present disclosure provides crystalline valbenazine, processes for preparing crystalline valbenazine, and pharmaceutical compositions comprising crystalline valbenazine.

The present disclosure also relates to the use of crystalline valbenazine disclosed herein for the preparation of a medicament, preferably for the treatment of hyperkinetic disorders.

The present invention further provides a pharmaceutical composition comprising crystalline valbenazine of the present disclosure and at least one pharmaceutically acceptable excipient.

The present invention also provides a method of treating hyperkinetic disorders, comprising administering a therapeutically effective amount of crystalline valbenazine of the present disclosure, or at least one of the above pharmaceutical compositions to a person suffering from a hyperkinetic disorder.

DETAILED DESCRIPTION OF THE DISCLOSURE

Figure 1:
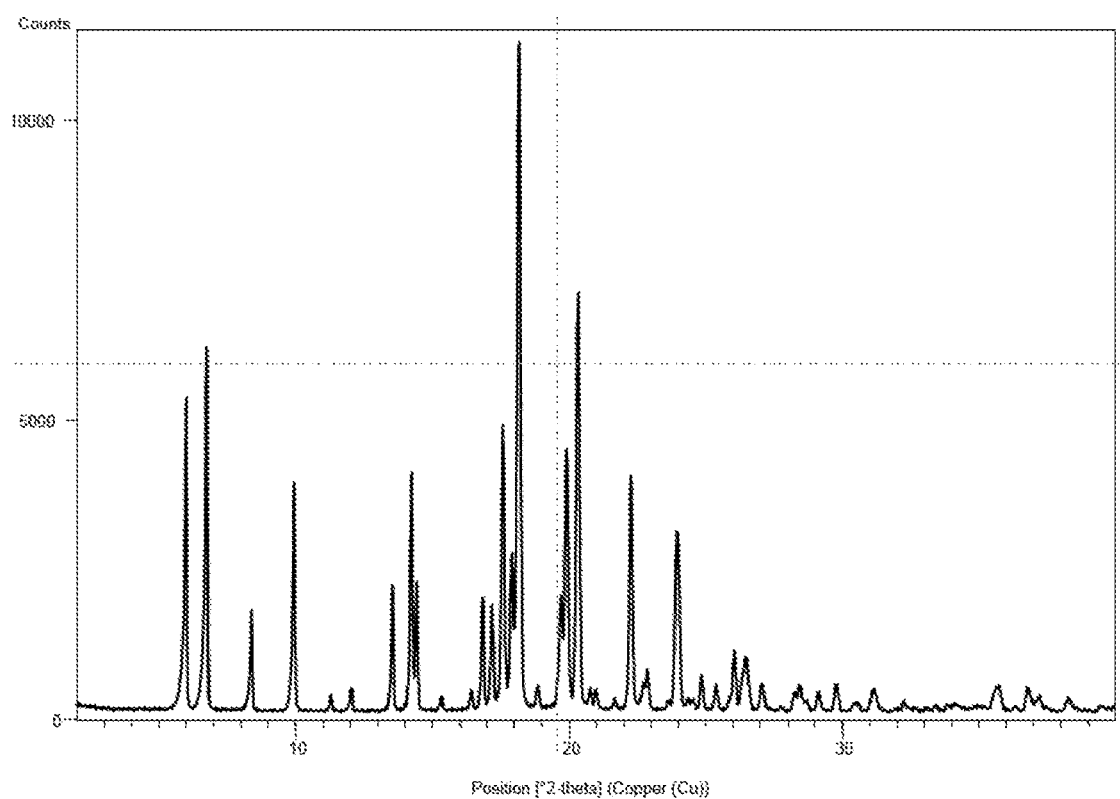
FIG. 1. illustrates the x-ray powder diffraction pattern (XRPD) [powder x-ray diffraction—PXRD] of crystalline valbenazine free base when measured at 22° C. and using Cu Kα radiation.

WO 2008/058261 A1 discloses the production of valbenazine (compound 2-1 in Example 2). Example 6 further discloses a composition formulated as liquid solution which is often inconvenient or even unacceptable for use in a pharmaceutical product. In contrast, WO 2015/171802 A1 discloses oral administration of valbenazine to patients (Example 2). According to page 16, lines 16-17 of the document, valbenazine is preferably used in form of its dihydrochloride or ditosylate salt. In contrast, the present invention relates to crystalline valbenazine as free base, which is suitable for use in a pharmaceutical product. Crystalline valbenazine free base is described and characterized herein.

The present disclosure provides crystalline valbenazine that has one or more desireable properties, inparticular compared to other solid state forms of valbenazine. In particular, the advantageous properties can be selected from the group consisting of chemical purity, flowability, solubility, dissolution rate, crystal morphology, polymorphic stability, thermal stability, mechanical stability, storage stability, a low content of residual solvent, a lower degree of hygroscopicity, flowability, and advantageous processing and handling characteristics such as compressibility and bulk density.

Abbreviations

PXRD powder X-ray diffractogram
XRPD X-ray powder diffraction
DSC differential scanning calorimetry
TGA thermogravimetric analysis
GMS gravimetric moisture sorption
THF tetrahydrofuran
MTBE methyl tert-butyl ether
RH relative humidity
Mp melting point
Definitions The term "valbenazine" as used herein refers to (S)-2-Amino-3-methyl-butyric acid, (2R,3R,11bR)-3-isobutyl-9,10-dimethoxy-1,3,4,6,7,11b-hexahydro-2H-pyrido[2,1-a]isoquinolizin-2-yl ester according to formula (I) disclosed herein above. A process for the preparation is disclosed in Examples 1 and 2 of WO 2008/058261 A1, incorporated herein by reference. Valbenazine (INN/USAN, also known as Ingrezza; NBI-98854; MT-5199) is a selective vesicular monoamine transporter (VMAT) 2 inhibitor which is effective in regulating presynaptic release of dopamine, for the potential treatment of central nervous system (CNS) indications, including hyperkinetic movement disorders such as tardive dyskinesia and Huntington's disease. Neurocrine Biosciences and Asia licensee Mitsubishi Tanabe are developing valbenazine. In August 2016, Neurocrine submitted an NDA in the US for tardive dyskinesia. The drug is also being developed in other indications, including Tourette syndrome. In October 2015, a phase II study (T-Forward) was initiated in adults with Tourette syndrome; in January 2016, a phase II trial (T-Force GREEN) in children and adolescents was initiated.

The term "valbenazine free base" as used herein refers to the solid form of valbenazine, having a chemical structure, wherein the molecule of valbenazine is not associated with any acid molecule.

Deuterium (2H or D) is a stable and non-radioactive isotope of hydrogen which has approximately twice the mass of protium (1H or H), the most common isotope of hydrogen. Deuteration of pharmaceuticals to improve pharmacokinetics (PK), pharmacodynamics (PD), and toxicity profiles has been demonstrated previously with some classes of drugs. As used herein, the term "valbenazine free base" also refers to the compound which is represented by the chemical structure as depicted in Formula IV or VI of the present invention, i.e. at least one of the protiums of the dimethoxy groups of the compound can be substituted by deuterium.

The term "is/are deuterium" when used to describe a given position in a molecule such as R or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "deuterated valbenazine" refers to the compound with the chemical name (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester, which is represented by the chemical structure as depicted in Formula I of the present invention, wherein the 9,10-dimethoxy groups are enriched with deuterium, i.e. at least one of the protiums of the dimethoxy groups is substituted by deuterium. Preferably, the deuterium enrichment is no less than about 98% of deuterium at this position.

The term "drugable form (of valbenazine)" as used herein is defined as any form (salt, amorphous, crystal, solution, dispersion, mixture etc.) that valbenazine might take which still can be formulated into a pharmaceutical formulation usable as a medicament to treat a disease or a symptom.

As used herein, the term "measured at a temperature in the range of from 20 to 30° C." refers to a measurement under standard conditions. Typically, standard conditions mean a temperature in the range of from 20 to 30° C., i.e. at room temperature. Standard conditions can mean a temperature of about 22° C. Standard conditions can also mean a temperature of about 25° C. Typically, standard conditions can additionally mean a measurement under 20-80% relative humidity, preferably 30-70% relative humidity, more preferably 40-60% relative humidity and most preferably 50% relative humidity.

As used herein the term "room temperature" refers to a temperature in the range of from 20 to 30° C.

The term "reflection" with regards to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms, whereas short-range order is over a few atoms only (see "*Fundamentals of Powder Diffraction and Structural Characterization of Materials*" by Vitalij K. Pecharsky and Peter Y. Zavalij, Kluwer Academic Publishers, 2003, page 3).

The term "essentially the same" with reference to powder X-ray diffraction means that variabilities in reflection positions and relative intensities of the reflections are to be taken into account. For example, a typical precision of the 2-Theta values is in the range of ±0.2° 2-Theta, preferably in the range of ±0.1° 2-theta. Thus, a reflection that usually appears at 7.3° 2-Theta for example can appear between 7.1° and 7.5° 2-theta, preferably between 7.2 and 7.4° 2-Theta on most X-ray diffractometers under standard conditions. Furthermore, one skilled in the art will appreciate that relative reflection intensities will show inter-apparatus variability as well as variability due to degree of crystallinity, preferred orientation, sample preparation and other factors known to those skilled in the art and should be taken as qualitative measure only.

As used herein, the term "substantially pure" with reference to a particular physical form means that the physical form includes at most 20%, preferably at most 10%, more preferably at most 5%, even more preferably at most 3% and most preferably at most 1% by weight of any other physical form of the compound.

The terms "physical form" and "solid form" are used interchangeably herein and refer to any crystalline and/or amorphous phase of a compound.

A crystalline solid form of valbenazine may be referred to herein as being characterized by graphical data "as shown in" a figure. Such data include, for example, PXRDs, DSCs, TGAs and GMS isotherms. The person skilled in the art understands that factors such as variations in instrument type, response and variations in sample directionality, sample concentration, sample purity, sample history and sample preparation may lead to variations for such data when presented in graphical form, for example variations relating to the exact peak positions and intensities. However, a comparison of the graphical data in the figures herein with the graphical data generated for an unknown physical form and the confirmation that two sets of graphical data relate to the same crystal form is well within the knowledge of a person skilled in the art.

The presence of more than one polymorph in a sample may be determined by techniques such as x-ray powder diffraction (PXRD) or solid state nuclear magnetic resonance spectroscopy. For example, the presence of extra peaks in the comparison of an experimentally measured PXRD pattern with a simulated PXRD pattern may indicate more than one polymorph in the sample. The simulated PXRD may be calculated from single crystal x-ray data. see Smith, D. K., "*A FORTRAN Program for Calculating X-Ray Powder Diffraction Patterns*," Lawrence Radiation Laboratory, Livermore, Calif., UCRL-7196 (April 1963) or TOPAS program (Total Pattern Analysis Solution, available through Brucker AXS Inc.).

As used herein, the term "mother liquor" refers to the solution remaining after crystallization of a solid.

The term "non-hygroscopic" as used herein refers to a compound which shows a water uptake of at most 0.5 weight %, based on the weight of the compound, when measured with gravimetric moisture sorption at a relative humidity in the range of from 0 to 95% and a temperature of 25.0±0.1° C.

The term "anhydrous" as used herein, refers to a solid, where no water is coordinated in or accommodated by the crystal structure. However, an anhydrate may still comprise residual water due to surface adsorption, solvent inclusions and/or absorption in disordered regions.

The term "solvate" as used herein, refers to a solid, where one or more organic solvent(s) is/are coordinated in or accommodated by the crystal structure.

The term "isostructural solvate" as used herein, refers to solvates having the same space group with only small distortions of the unit cell dimensions and the same type of molecular network of the host molecule. Isostructural solvates as defined herein, only differ in the type of organic solvent present as guest molecule.

The term "desolvating" as used herein, means the at least partial removal of organic solvent from the crystal structure of the host molecule.

"Reduced pressure" as used herein means a pressure in the range of from 10 mbar to 900 mbar.

As used herein, the term "about" means within a statistically meaningful range of a value. Such a range can be within an order of magnitude, typically within 10%, more typically within 5%, even more typically within 1% and most typically within 0.1% of the indicated value or range. Sometimes, such a range can lie within the experimental error, typical of standard methods used for the measurement and/or determination of a given value or range.

The term "pharmaceutically acceptable acid addition salt" as used herein means any acid addition salt ov valbenazine which retains valbenazines biological properties and which is not toxic or otherwise undesireable for pharmaceutical use. Such salts include, but are not limited to, acid addition salts formed with inorganic acids, such as hydrochloric, hydrobromic, sulfuric, nitric or phosphoric acid, to name but a few, or salts formed with organic acids, such as acetic, citric, malonic, tartaric, methanesulfonic, camphorsulfonic or p-toluene-sulfonic acid, to name but a few.

Preparation of Crystalline Materials

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

Crystals of drugs, including polymorphs, methods of preparation, and characterization of drug crystals are discussed in *Solid-State Chemistry of Drugs*, S. R. Byrn, R. R. Pfeiffer, and J. G. Stowell, 2$^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be comilled or passed through a mesh screen to delump the product, if necessary.

Preferred processes for the preparation of the crystalline solid forms of valbenazine of the invention are provided in the examples and in the embodiment sections, respectively.

Valbenazine free base can be prepared according to the procedure disclosed in WO 2008/058261 A1. Valbenazine free base is then crystallized, for example by using a solvent system as described in example 1 or 2 or items 12 to 15. In the process of WO 2008/058261 A1 the coupling agent dicyclohexylcarbodiimide can be substituted by another suitable coupling agent, such as for example N-(3-dimethylaminopropyl)-N'-ethylcarbodiimide (EDC).

Once the crystalline solid form of valbenazine free base is obtained in essentially pure form, at least a part of the crystals are separated from their mother liquor. Preferably, the crystals are separated from their mother liquor by any conventional method such as filtration, centrifugation, solvent evaporation or decantation, more preferably by filtration or centrifugation and most preferably by filtration. Optionally, in a further step the isolated crystals are washed with a suitable solvent, for example diethyl ether. The obtained crystals may optionally be dried.

Alternatively, deuterated valbenazine can be used as the starting material for crystallization. This compound is e.g. disclosed in WO 2014/120654 and can be prepared according to the methods disclosed therein. In general, deuterated valbenazine can be produced by providing tetrabenazine or deutetrabenazine (WO 2010/044981, WO 2011/153157, WO 2015/084622) followed by reduction of the ketone to the corresponding alcohol, conjugation with N-protected L-valine and final removal of the N-protecting group. Alternatively, deuterated valbenazine can be accessed starting from (+)-tetrabenazine via selective removal of the methoxy group under acidic conditions (see Brossi et al. Helvetica Chimica Acta (1958), 16, p. 119f) followed by alkylation with a deuterated methylating agent such as D3Cl or (D3CO)2SO2, followed by the final assembly.

The present inventors have further found that crystalline valbenazine free base and crystalline deuterated valbenazine free base are useful intermediates for the preparation of pharmaceutically acceptable acid addition salts of valbenazine or deuterated valbenazine, such as valbenazine ditosylate or deuterated valbenazine ditosylate. The present invention therefore also relates to a process for the preparation of a pharmaceutically acceptable salt of valbenazine, such as valbenazine ditosylate, comprising the step of crystallizing valbenazine free base.

WO 2017/112857 A1 describes a process for the preparation of valbenazine ditosylate. The final steps of the synthesis, described in example E and F on pages 57 and 58 are deprotection of the BOC-group, crystallization of the dihydrochloride salt of valbenazine, preparation of a valbenazine free base solution from the dihydrochloride with aqueous sodium bicarbonate and the addition of p-toluene-sulfonic acid and crystallization of the ditosylate.

The current process is faster and less cumbersome, because it omits the detour via the crystalline dihydrochloric acid salt. After deprotection of the BOC-group the valbenazine free base is crystallized directly and then crystalline valbenazine free base is used as the starting material for the preparation of a crystalline pharmaceutically acceptable salt of valbenazine or deuterated valbenazine, such as the valbenazine ditosylate.

The present invention therefore also relates to the use of crystalline valbenazine free base, such as crystalline valbenazine free base according to any one of items 1 to 5 or crystalline deuterated valbenazine free base according to any one of items 16 to 18 below, for the preparation of a pharmaceutically acceptable acid addition salt of valbenazine or deuterated valbenazine. Preferably for the preparation of a crystalline pharmaceutically acceptable acid addition salt of valbenazine or deuterated valbenazine, such as crystalline valbenazine ditosylate or crystalline deuterated valbenazine ditosylate.

The present invention also relates to a process for the preparation of a pharmaceutically acceptable salt of valbenazine, such as valbenazine ditosylate, wherein
- a) crystalline valbenazine free base is dissolved in a solvent,
- b) the valbenazine free base is brought into contact with a pharmaceutically acceptable acid, and
- c) a solid form of the pharmaceutically acceptable acid addition salt of valbenazine is isolated.

Preferably the solid form of the pharmaceutically acceptable acid addition salt of valbenazine is a crystalline solid form. A preferred pharmaceutically acceptable acid addition salt of valbenazine is a sulfonic acid addition salt, for example valbenazine ditosylate.

The solvent in step a) is not particularly limited. Preferred solvents for step a) are solvents which allow easy crystallization of the valbenazine acid addition salts in step c). In the case where valbenazine ditosylate is to be prepared, acetonitrile, diisopropylether, diethylether and toluene have given good results and allowed the preparation of crystalline valbenazine ditosylate.

Aspects, advantageous features and preferred embodiments of the present invention are summarized in the following items 1. Crystalline valbenazine.
2. The crystalline valbenazine according to claim 1, in substantially pure form.
3. The crystalline valbenazine according to any one of items 1 or 2, characterized by a x-ray powder diffraction pattern comprising four or more 2θ values selected from the group consisting of 6.0±0.2°, 6.8±0.2°, 8.4±0.2°, 10.0±0.2°, 14.2±0.2°, 17.6±0.2°, 18.2±0.2° and 20.3±0.2°, when measured at a temperature of about 22° C. using Cu Kα radiation.
4. The crystalline valbenazine according to item 3, having a X-ray diffraction spectrum substantially the same as the X-ray powder diffraction spectrum shown in FIG. 1.
5. The crystalline valbenazine according to any one of items 1 to 4 having a melting and/or decomposition temperature between 90° C. and 95° C.
6. A composition comprising at least 95 weight % of crystalline valbenazine according to any one of items 1 to 6, based the weight of the composition.
7. The composition of item 6 consisting essentially of the crystalline form of any one of items 3 to 5.
8. A pharmaceutical composition comprising crystalline valbenazine according to any one of items 1 to 5 or the composition according to any one of items 6 or 7, and a pharmaceutically acceptable carrier or diluent.
9. A method of treating a hyperkinetic movement disorder in a human comprising administering to the human a therapeutically-effective amount of the pharmaceutical composition according to item 8.
10. A pharmaceutical composition according to item 8 for use in the treatment of a hyperkinetic movement disorder in a human.
11. The method of treating a hyperkinetic movement disorder according to item 9, or the pharmaceutical composition for use in the treatment of a hyperkinetic movement disorder according to item 10, wherein the hyperkinetic movement disorder is tardive dyskinesia or Tourette syndrome.
12. A process of making crystalline valbenazine according to any one of items 1 to 5 or the composition according to any one of items 6 or 7, comprising: allowing valbenazine to crystallize from a solvent comprising diethylether.
13. The process according to item 12, wherein the solvent further comprises isopropylalcohol, dichloromethane, methylethylketone, cyclohexanone, ethylacetate or cyclohexane.
14. The process according to any one of item 12 or 13, further comprising the step of carbon filtering, preferably under exclusion from light.
15. The process according to any one of items 12 to 14, wherein valbenazine is allowed to crystallize at a temperature of from 0° C. to 40° C.
16. The crystalline valbenazine according to any one of items 1 to 5, wherein the valbenazine is deuterated valbenazine.
17. The crystalline deuterated valbenazine according to item 16, wherein in at least one of the 9,10-dimethoxy groups of deuterated valbenazine all hydrogen positions are enriched with deuterium, i.e. wherein in at least one of the 9,10-dimethoxy groups of deuterated valbenazine all of the protiums of the dimethoxy groups are substituted by deuterium.
18. The crystalline deuterated valbenazine according to items 16 or 17, wherein in both of the 9,10-dimethoxy groups of deuterated valbenazine all hydrogen positions are enriched with deuterium, i.e. wherein in both of the 9,10-dimethoxy groups of deuterated valbenazine all of the protiums of the dimethoxy groups are substituted by deuterium.
19. A composition comprising at least 95 weight % of crystalline deuterated valbenazine according to any one of items 16 to 18, based the weight of the composition.
20. The composition of item 19 consisting essentially of the crystalline form of any one of items 16 to 18.
21. A pharmaceutical composition comprising crystalline deuterated valbenazine according to any one of items 16 to 18 or the composition according to any one of items 19 or 20, and a pharmaceutically acceptable carrier or diluent.
22. A method of treating a hyperkinetic movement disorder in a human comprising administering to the human a therapeutically-effective amount of the pharmaceutical composition according to item 21.
23. A pharmaceutical composition according to item 21 for use in the treatment of a hyperkinetic movement disorder in a human.
24. The method of treating a hyperkinetic movement disorder according to item 22, or the pharmaceutical composition for use in the treatment of a hyperkinetic movement disorder according to item 23, wherein the hyperkinetic movement disorder is tardive dyskinesia or Tourette syndrome.
25. A process of making crystalline deuterated valbenazine according to any one of items 16 to 18 or the composition according to any one of items 19 or 20, comprising:
allowing deuterated valbenazine to crystallize from a solvent comprising diethylether.

26. The process according to item 25, wherein the solvent further comprises isopropylalcohol, dichloromethane, methylethylketone, cyclohexanone, ethylacetate or cyclohexane.

27. The process according to any one of item 25 or 26, further comprising the step of carbon filtering, preferably under exclusion from light.

28. The process according to any one of items 25 to 27, wherein deuterated valbenazine is allowed to crystallize at a temperature of from 0° C. to 40° C.

The pharmaceutical composition may be prepared by pharmaceutical standard procedures e.g. by wet or dry processing methods, with dry processing methods being preferred. The pharmaceutical composition is preferably prepared by dry processing methods, such as, but not limited to, direct compression or dry granulation methods. An example of dry granulation is roller compaction. The pharmaceutical composition obtained by dry or wet processing methods are preferably compressed into tablets or encapsulated.

In a further aspect the invention relates to a pharmaceutical composition comprising crystalline valbenazine freebase, such as crystalline deuterated valbenazine free base, as defined above or the composition comprising the same as defined above and at least one pharmaceutically acceptable excipient. Preferably, the at least one pharmaceutically acceptable excipient is/selected from the group consisting of of binders, fillers, diluents, disintegrants, lubricants, glidants, coloring agents, flavouring agents, sweetening agents, emulsifying agents, dispersing agents, wetting agents and film coatings.

In one embodiment, suitable binders which may be used for the pharmaceutical composition of the present invention include, but are not limited to starches such as corn starch, potato starch and pre-gelatinized starch (e.g. STARCH 1500); gelatin, sugars such as sucrose, glucose, dextrose, molasses and lactose; natural and synthetic gums such as acacia, alginic acid, alginates, extract of irish moss, panwar gum, ghatti gum, mucilage of isabgol husks, carboxymethylcellulose, methylcellulose; polyinylpyrrolidone (PVP), veegum, larch arabogalactan, powdered tragacanth and guar gum; celluloses such as ethyl cellulose, cellulose acetate, carboxymethyl cellulose calcium, sodium carboxymethyl cellulose, methyl cellulose, hydroxyethyl cellulose (HEC), hydroxypropylcellulose (HPC), hydroxypropyl methyl cellulose (HPMC); microcrystalline celluloses such as AVICEL-PH-101, AVICEL-PH-103, AVICEL RC-581, AVICEL-PH-105 (FMC Corp., Marcus Hook, Pa.); and mixtures thereof.

In another embodiment, suitable fillers which may be used for the pharmaceutical composition of the present invention include, but are not limited to talc, calcium carbonate, microcrystalline cellulose, powdered cellulose, dextrates, kaolin, mannitol, silicic acid, sorbitol, starch, pregelatinized starch, and mixtures thereof.

In another embodiment, suitable diluents which may be used for the pharmaceutical composition of the present invention include, but are not limited to dicalcium phosphate, calcium sulfate, lactose, sucrose, inositol, cellulose, kaolin, mannitol, sodium chloride, dry starch and powdered sugar.

In a further embodiment, suitable disintegrants which may be used for the pharmaceutical composition of the present invention include, but are not limited to agar, bentonite, celluloses such as methylcellulose and carboxymethylcellulose; wood products; natural sponge; cation-exchange resins; alginic acid; gums such as guar gum and Vee gum HV; citrus pulp; cross-linked celluloses such as crosscarmellose; cross-linked polymers such as crospovidone; cross-linked starches; calcium carbonate; microcrystalline cellulose; sodium starch glycolate; polacrilin potassium; starches such as corn starch, potato starch, tapioca starch and pregelatinized starch; clays; aligns; and mixtures thereof;

In still a further embodiment, suitable lubricants which may be used for the pharmaceutical composition of the present invention include, but are not limited to calcium stearate, magnesium stearate, mineral oil, light mineral oil, glycerin, sorbitol, mannitol, glycols such as glycerol behenate and polyethylene glycol (PEG); stearic acid, sodium laryl sulfate, talc, hygrogenated vegetable oil including, peanut oil, cottonseed oil, sunflower oil, sesame oil, olive oil, corn oil and soybean oil; zinc stearate, ethyl oleate, ethyl laureate, agar, starch, lycopodium, silica or silica gels such as AEOROSIL® 200 (W.R. Grace Co., Baltimore, Md.) and CAB-O-SIL® (Cabot Co. of Boston, Mass.); and mixtures thereof In even a further embodiment, suitable glidants which may be used for the pharmaceutical composition of the present invention include, but are not limited to colloidal silicon dioxide, CAB-O-SIL® (Cabot Co. of Boston, Mass.) and asbestos-free talc.

It should be understood that many excipients may serve several functions, event within the same formulation.

In one embodiment, the present invention relates to a pharmaceutical composition as defined above, wherein the predetermined and/or pharmaceutically effective amount of crystalline valbenazine free base, such as crystalline deuterated free base of the present invention is in the range of from about 5 to 150 mg, calculated as water free valbenazine. Preferably, the predetermined and/or pharmaceutically effective amount of the crystalline valbenazine free base of the present invention is selected from the group consisting of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg and 150 mg, calculated as water free valbenazine. More preferably, the predetermined and/or pharmaceutically effective amount of the crystalline valbenazine free base of the present invention is selected from the group consisting of 25 mg, 40 mg, 50 mg, 75 mg, 80 mg and 100 mg, calculated as water free valbenazine. Even more preferably, the predetermined and/or pharmaceutically effective amount of the crystalline valbenazine free base of the present invention is 40 or 80 mg, most preferably 40 mg, calculated as water free valbenazine.

In one embodiment, the invention relates to a pharmaceutical composition as defined above, which is an oral solid dosage form. Preferably, the oral solid dosage form is a capsule or a tablet, more preferably a tablet and most preferably a film-coated tablet.

Preferably, the present invention relates to a pharmaceutical composition as defined above, wherein the pharmaceutical composition is to be administered once-daily.

In still another aspect the invention relates to the pharmaceutical composition as defined above for use as a medicament.

In a further aspect the invention relates to the pharmaceutical composition as defined above for use in the treatment of hyperkinetic disorders. In a preferred embodiment, the hyperkinetic disorder is tardive dyskinesia.

In a preferred embodiment of the present invention the dosage form of the present invention is packed by a suitable packaging material. The packaging material preferably reduces or prevents water exchange between the pharmaceutical composition of the present invention and the environment. For example, if the dosage forms are tablets or capsules, suitable blister pack materials can be used. The blister pack may comprise a cavity or pocket, preferably containing a thermoformed plastic. This usually has as a backing a lidding seal containing an aluminum and/or plastic foil. Further, if the composition is in form of a granulate, suitable sachets can be used.

In a particularly preferred embodiment the pharmaceutical composition or the dosage form of the present invention is packed by a material having a water vapor permeability of 0.001 to 0.15 g/m²/day at 38° C./5%/90% RH, preferably of 0.01 to 0.12 g/m²/day at 38° C./5%/90% RH, in particular 0.05 to 0.10 g/m²/day at 38° C./5%/90% RH, wherein said water vapor permeability is determined according to ASTM F1249-13. Preferably, a Permatran-W Model 3/33 device is used. The measurement is preferably carried out at 38° C. Further, preferably the humidity in the dry chamber is 5% relative humidity (=RH), whereas the humidity in the wet chamber is 90% RH.

In a preferred embodiment the packaging material can preferably be selected from polyvinylchloride (PVC), polyvinylidene chloride (PVDC), polyethylene (PE), polypropylene (PP), polyethylene terephthalate (PET) polystyrol (PS), polyamide and alumina or combinations thereof. Alu/Alu blisters are particularly preferred.

In a preferred embodiment the packing material comprises layered sheets, which can be thermoformed, containing one or more layers. In a preferred embodiment the packing material can be a composite material, e.g. co-extruded composite material, e.g. a polyamide-alumina-polyvinyl chloride composite material, which is also referred to as Nylon®-Alu-PVC.

In a preferred embodiment the packaging material has a thickness of 1 µm to 1 mm. In case of a blister pack the thermoformed plastic pocket preferably has a thickness of 100 to 1000 µm, more preferably of 150 to 800 µm. Further, the backing foil usually has a thickness of 10 to 150 µm, more preferably of 15 to 100 µm.

EXAMPLES

Example 1

For the purpose of the present invention, valbenazine free base was produced as follows:

Tetrabenazine rac., 99% (333.0 g, 1 mol) was suspended in acetone (4 L). The resulting white suspension was warmed in a water bath until complete dissolution was observed (internal temperature 31° C.). (1S)-(+)-10-camphorsulfonic acid (243.7 g, 1 mol) was then added to the solution. On complete addition the resulting mixture was cooled to 16° C. and stirred for 24 h. A small amount of seed crystal was added and the solution became turbid. After ageing for 48 h the resulting suspension was filtered and washed with acetone (3×150 mL) to give 500 g of colourless solid. The mother liquor and the solid were then recombined and the mixture dissolved in acetone (8 L) under reflux. 500 mL of the resulting clear yellow solution was separated from the main batch and allowed to cool to room temperature. After room temperature was reached the solution was cooled to 15° C. at which point turbidity was observed. Stirring was continued overnight at 15° C. The thick suspension was filtered to give 63 g of solid which was washed with acetone (3×50 mL) to give (3R,11bR)-3-Isobutyl-9,10-dimethoxy-1, 3,4,6,7,11b-hexahydropyrido[2,1-a]isoquinolin-2-one*(S)-(+)CSA (30 g, 99%, ee). The remaining 7.5 L of acetone solution from the bulk material was processed the same way to provide an additional 150 g of material of the same grade.

(3R,11bR)-3-Isobutyl-9,10-dimethoxy-1,3,4,6,7,11b-hexahydropyrido[2,1-a]isoquinolin-2-one*(S)-(+) CSA (151 g) was vigorously stirred in a mixture of water (2 L, adjusted to pH 8 with Na$_2$CO$_3$) and Et$_2$O (2.5 L) until all solids were dissolved. Stirring was stopped and the organic layer was separated and dried. The ether was removed in vacuo to provide (3R,11bR)-tetrabenazine (83.12 g). The colourless solid was dissolved in THF (1.5 L) and the clear solution was cooled to −20° C. Borane dimethylsulfide complex (2M solution in THF) was then added in a dropwise manner while keeping the internal temperature at −20° C. The reaction was stirred for 2.5 hours and quenched with aqueous ammonia, 35% (750 mL). The resulting mixture was stirred at 35° C. overnight. Brine (800 mL) and Et$_2$O (800 mL) were added, the organic layer separated and the ether removed in vacuo to afford a colourless foam (93.4 g). This material was dissolved in acetone (400 mL) and water (1.2 L) was then added resulting in a suspension. After filtration, the crude product was washed with acetone/water (1:5) and dried in vacuo to give (2R,3R,11bR)-3-isobutyl-9,10-dimethoxy-1,3,4,6,7,11b-hexahydro-2H-pyrido[2,1-a] isoquinolin-2-ol as a white solid (75 g).

(2R,3R,11bR)-3-Isobutyl-9,10-dimethoxy-1,3,4,6,7,11b-hexahydro-2H-pyrido[2,1-a]isoquinolin-2-ol (75 g, 235 mmol) was dissolved in 1 L anhydrous CH$_2$Cl$_2$ along with DMAP (28.7 g, 235 mmol) and benzyloxycarbonyl-L-valine (70.8 g, 282 mmol). The mixture was stirred for 5 min and DCC (58.1 g, 282 mmol) was added in a portionwise manner, resulting in a yellow solution which became turbid on standing. The mixture was stirred overnight and then filtered, washed with dichloromethane and concentrated. Purification via flash column chromatography gave 95.7 g (S)-2-benzyloxycarbonyl-amino-3-methyl-butyric acid-(2R, 3R,11bR)-3-isobutyl-9,10-dimethoxy-1,3,4,6,7,11b-hexahydro-2H-pyrido[2,1-a]isoquinolin-2-yl ester as a pale yellow solid.

Pd/C (10 g) was placed under an atmosphere of nitrogen and enough methanol was added to cover the solid completely. The ester product (95 g, 172 mmol) was dissolved in MeOH (2 L) and added to the catalyst slurry. The mixture was placed under vacuum and purged twice with nitrogen before being finally purged with H$_2$. The mixture was stirred overnight, filtered through celite and dried in vacuo. The crude product was dissolved in Et$_2$O (300 mL) and n-hexane (300 mL). The solution was concentrated at 41° C. under reduced pressure (700 mbar). Cooling the concentrated solution with an ice bath produced a white solid. The crystals were washed with n-hexane and purified via flash column chromatography (0.5:9.5, MeOH:CH$_2$Cl$_2$) to give 59 g of valbenazine free base.

Example 2

Valbenazine free base (4 g) prepared as per Example 1, was dissolved in dry diethyl ether (80 mL). The resulting turbid mixture was then stirred for 30 min and filtered through a 0.44 micron PVDF (Polyvinyldienefluoride) filter and concentrated to dryness under under vacuum (600 mbar). The resulting pale yellow amorphous solid is dissolved in 30 mL cyclohexane and refluxed for 1 min to obtain a clear solution which was filtered through charcoal to remove the yellow coloration. The resulting colourless solution was protected from light and allowed to crystallise at room temperature for 24 h. The resulting solid (50% yield) was filtered and air dried under vacuum for 2 h.

Example 3

The X-ray powder diffraction patterns (XRPD) of the compound of example 2 were obtained with a X'Pert PRO diffractometer (PANalytical, Almelo, The Netherlands) equipped with a theta/theta coupled goniometer in transmission geometry, programmable XYZ stage with well plate holder, Cu-Kα1,2 radiation source (wavelength 0.15419 nm) with a focussing mirror, a 0.5° divergence slit, a 0.02° soller slit collimator and a 0.5° anti-scattering slit on the incident beam side, a 2 mm anti-scattering slit, a 0.02° soller slit collimator, a Ni-filter and a solid state PIXcel detector on the diffracted beam side. The patterns were recorded at a tube voltage of 40 kV, tube current of 40 mA, applying a stepsize of 0.013° 2θ with 40 s per step in the angular range of 2° to 40° 2θ.

Significant peaks were observed at the following positions [±0.2° 2Th.] (Table 1 and FIG. 1):

| No. | Pos. [°2Th.] | d-spacing [Å] | Rel. Int. [%] |
|---|---|---|---|
| 1 | 6.01 | 14.718 | 47 |
| 2 | 6.75 | 13.091 | 54 |
| 3 | 8.39 | 10.538 | 15 |
| 4 | 9.95 | 8.887 | 34 |
| 5 | 11.30 | 7.832 | 2 |
| 6 | 12.04 | 7.348 | 3 |
| 7 | 13.54 | 6.538 | 19 |
| 8 | 14.24 | 6.221 | 36 |
| 9 | 14.44 | 6.135 | 19 |
| 10 | 15.34 | 5.775 | 2 |
| 11 | 16.44 | 5.394 | 3 |
| 12 | 16.84 | 5.264 | 17 |
| 13 | 17.20 | 5.157 | 16 |
| 14 | 17.59 | 5.043 | 43 |
| 15 | 17.92 | 4.951 | 23 |
| 16 | 18.17 | 4.881 | 100 |
| 17 | 18.86 | 4.705 | 4 |
| 18 | 19.72 | 4.503 | 17 |
| 19 | 19.92 | 4.458 | 39 |
| 20 | 20.34 | 4.366 | 61 |
| 21 | 20.78 | 4.275 | 3 |
| 22 | 20.99 | 4.232 | 3 |
| 23 | 22.27 | 3.992 | 35 |
| 24 | 22.73 | 3.912 | 4 |
| 25 | 22.87 | 3.888 | 6 |
| 26 | 23.97 | 3.712 | 26 |
| 27 | 24.85 | 3.583 | 5 |
| 28 | 25.38 | 3.509 | 4 |
| 29 | 26.05 | 3.420 | 9 |
| 30 | 26.32 | 3.387 | 4 |
| 31 | 26.47 | 3.367 | 8 |
| 32 | 27.06 | 3.295 | 4 |
| 33 | 28.27 | 3.157 | 3 |
| 34 | 28.44 | 3.139 | 4 |
| 35 | 29.14 | 3.065 | 3 |
| 36 | 29.78 | 3.000 | 4 |
| 37 | 31.16 | 2.871 | 3 |
| 38 | 35.70 | 2.513 | 4 |
| 39 | 36.79 | 2.441 | 4 |

Particularly selected peaks were observed at the following positions [±0.2° 2Th.] (Table 2):

| Pos. [°2Th.] | d-spacing [Å] |
|---|---|
| 6.01 | 14.718 |
| 6.75 | 13.091 |
| 8.39 | 10.538 |
| 9.95 | 8.887 |
| 14.24 | 6.221 |
| 17.59 | 5.043 |
| 18.17 | 4.881 |
| 20.34 | 4.366 |

Example 4

Differential scanning calorimetry (DSC) was performed with a Diamond-DSC (Perkin-Elmer, Norwalk, Conn., USA) using a Pyris 2.0 software. Approximately 1 to 3±0.0005 mg sample (using a UM3 ultramicrobalance, Mettler, Greifensee, CH) was weighed into an Al-Pan (25 μl) and sealed with a cover, which was perforated by a needle. Dry nitrogen was used as the purge gas (purge: 20 ml*min-1).

Figure 2:
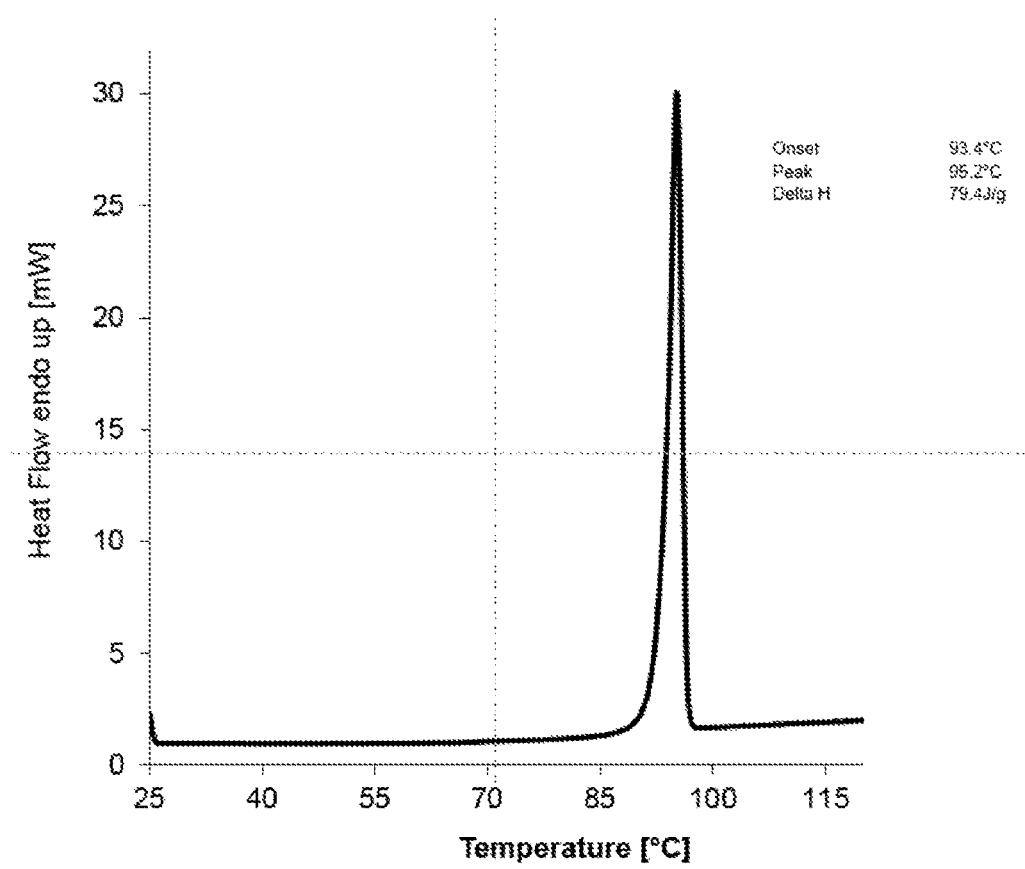
FIG. 2. illustrates the DSC thermogram of crystalline valbenazine free base.

The DSC thermogram of the compound of example 2 is displayed in FIG. 2.

What is claimed is:

1. Crystalline valbenazine characterized by an x-ray powder diffraction pattern comprising four or more 2θ values selected from the group consisting of 6.0±0.2°, 6.8±0.2°, 8.4±0.2°, 10.0±0.2°, 14.2±0.2°, 17.6±0.2°, 18.2±0.2° and 20.3±0.2°, when measured at a temperature of about 22° C. using Cu Kα radiation.

2. The crystalline valbenazine according to claim 1, in substantially pure form.

3. The crystalline valbenazine according to claim 1, having a X-ray diffraction spectrum substantially the same as the X-ray powder diffraction spectrum shown in FIG. 1.

4. The crystalline valbenazine according to claim 1 having a melting and/or decomposition temperature between 90° C. and 95° C.

5. A composition comprising at least 95 weight % of crystalline valbenazine according to claim 1, based the weight of the composition.

6. The composition of claim 5 consisting essentially of crystalline valbenazine characterized by a x-ray powder diffraction pattern comprising four or more 2θ values selected from the group consisting of 6.0±0.2°, 6.8±0.2°, 8.4±0.2°, 10.0±0.2°, 14.2±0.2°, 17.6±0.2°, 18.2±0.2° and 20.3±0.2°, when measured at a temperature of about 22° C. using Cu Kα radiation.

7. A process of making crystalline valbenazine according to claim 1, comprising:
   allowing valbenazine to crystallize from a solvent comprising diethylether.

8. The process according to claim 7, wherein the solvent further comprises isopropylalcohol, dichloromethane, methylethylketone, cyclohexanone, ethylacetate or cyclohexane.

9. The process according to claim 7, further comprising the step of carbon filtering.

10. The process according to claim 7, wherein valbenazine is allowed to crystallize at a temperature of from 0° C. to 40° C.

11. The process according to claim 7, further comprising reacting the crystalline valbenazine with a pharmaceutically acceptable acid to form a pharmaceutically acceptable acid addition salt of valbenazine.

* * * * *